United States Patent
Jenkins

(10) Patent No.: US 10,039,799 B2
(45) Date of Patent: Aug. 7, 2018

(54) PRINCESS LITE

(71) Applicant: Lillian Jenkins, Rocky Mount, NC (US)

(72) Inventor: Lillian Jenkins, Rocky Mount, NC (US)

( * ) Notice: Subject to any disclaimer, the term of this patent is extended or adjusted under 35 U.S.C. 154(b) by 260 days.

(21) Appl. No.: 15/215,130

(22) Filed: Jul. 20, 2016

(65) Prior Publication Data

US 2018/0021400 A1    Jan. 25, 2018

(51) Int. Cl.
| | |
|---|---|
| *A61K 36/8962* | (2006.01) |
| *A61K 36/47* | (2006.01) |
| *A61K 36/185* | (2006.01) |
| *A61K 38/12* | (2006.01) |
| *A61K 9/06* | (2006.01) |

(52) U.S. Cl.
CPC ............ *A61K 36/8962* (2013.01); *A61K 9/06* (2013.01); *A61K 36/185* (2013.01); *A61K 36/47* (2013.01); *A61K 38/12* (2013.01)

(58) Field of Classification Search
None
See application file for complete search history.

(56) References Cited

U.S. PATENT DOCUMENTS

2008/0260655 A1*   10/2008   Tamarkin ............... A61K 8/046
                                                                                                                                                             424/45

* cited by examiner

*Primary Examiner* — Susan Hoffman

(57) ABSTRACT

A non-invasive topical cream comprising 500 mg garlic, 1 tbs castor oil, 2 tbs virgin coconut oil, 2 tbs African shea butter, 1 tbs Pau D'Arco, and 1 tbs bacitracin for treating and managing breast health.

1 Claim, No Drawings

PRINCESS LITE

Princess Lite is a cream used to treat and manage breast health. It has been effective in dissolving cyst and tumors, benign and malignant, in the breast and other parts of the body. It begins working on first use. It is most effective when used together with heat therapy at least 1½-2 hours daily on inflicted site. It dissolved tumors within a two month period. However, it begins minimizing the tumors immediately.

THE FORMULA 500 mg garlic capsule
1 tbs castor oil
2 tbs virgin coconut oil
2 tbs african shea butter
1 tbs Pau D'Arco
1 tbs Bacitracin (Crushed pill or ointment)

Testimony:

I created this formula when I had a diagnosis of tumors found in the breast area, one at 12:00 and one at 6:00. I was devastated so I did some research of the ingredients I had at home. I prayerfully mixed these products and developed the cream. I immediately did heat therapy for 1½-2 hours a day to accelerate the effectiveness of the formula. I applied the cream 3 times a day (30 minute heat therapy per application). I put the cream around the known infected area, the nipple, the areola, and lymph nodes in my under arms. Within two months, the next ultrasound revealed that the tumors were gone. I did not inform my doctor that I had created this formula. I kept it to myself for some time. Then I informed a person with breast cancer about my formula and I gave her some of the cream. Her tumors were smaller and they dissolved within a month—she also used heat therapy. For her cream, I did not have any bacitracin crushed pills, so I went to the store and found an ointment form of bacitracin. After it proved to be effective on her, I was amazed. When a friend came to me and asked about the cream, I told her I was not sure if it would be effective for her situation. Her father had cancer in his intestines. But she took two cups of the cream and applied it to his inflicted area—also used heat therapy. Within three months his tumor was gone. I know there has to be something great about this formula. I feel it is time to present it.

The only side effect I did experience was some excessive itching on some days. To protect myself, in case I was allergic to an ingredient, I took an antihistamine so that the reaction would not be as severe. Within a month of using the cream, I did notice that in each breast, around the areola, I had developed two rather large brown spots. I started applying the cream there. It soon dissolved. The cream seems to pull the actual tumor forward and out.

Personal Facts:

I am currently a respiratory therapist and CEO of a home health company. Maneuvering to fix things and coming up with techniques to improve the effectiveness of therapy is what I am used to doing. I also have a sister that died from breast cancer. So when I was diagnosed with tumors, I was more aggressive in wanting to treat it. I really feel that this cream will save millions of lives. Many people do not understand the innovation and intelligence in our country when it comes to creating effective treatment ideas. The fact that it is something created in America is awesome. This will show to the world that we are innovative. I truly hope that this formula is researched so it can save millions of lives.

What is claimed is:

1. A non-invasive topical cream comprising 500 mg garlic, 1tbs castor oil, 2 tbs virgin coconut oil, 2 tbs African shea butter, 1 tbs Pau D'Arco, and 1 tbs bacitracin.

* * * * *